(12) United States Patent
Garrison et al.

(10) Patent No.: US 10,441,352 B2
(45) Date of Patent: *Oct. 15, 2019

(54) SWITCH ASSEMBLIES FOR MULTI-FUNCTION SURGICAL INSTRUMENTS AND SURGICAL INSTRUMENTS INCORPORATING THE SAME

(71) Applicant: COVIDIEN LP, Mansfield, MA (US)

(72) Inventors: David M. Garrison, Longmont, CO (US); Dylan R. Kingsley, Broomfield, CO (US); Tony Moua, Broomfield, CO (US)

(73) Assignee: COVIDIEN LP, Mansfield, MA (US)

( * ) Notice: Subject to any disclaimer, the term of this patent is extended or adjusted under 35 U.S.C. 154(b) by 287 days.

This patent is subject to a terminal disclaimer.

(21) Appl. No.: 15/459,934

(22) Filed: Mar. 15, 2017

(65) Prior Publication Data

US 2017/0189099 A1 Jul. 6, 2017

Related U.S. Application Data

(63) Continuation of application No. 14/280,834, filed on May 19, 2014, now Pat. No. 9,597,141.

(Continued)

(51) Int. Cl.
*A61B 18/14* (2006.01)
*A61B 18/12* (2006.01)
*A61B 18/00* (2006.01)

(52) U.S. Cl.
CPC .......... *A61B 18/1445* (2013.01); *A61B 18/12* (2013.01); *A61B 18/1206* (2013.01);

(Continued)

(58) Field of Classification Search
CPC ..... A61B 18/12; A61B 18/1206; A61B 18/14; A61B 18/1442; A61B 18/1445;

(Continued)

(56) References Cited

U.S. PATENT DOCUMENTS

| 5,312,391 A | 5/1994 | Wilk |
| 5,318,589 A | 6/1994 | Lichtman |

(Continued)

FOREIGN PATENT DOCUMENTS

DE 4242143 A1 6/1994

OTHER PUBLICATIONS

European Search Report from corresponding EP 14183014 dated Jan. 27, 2015.

(Continued)

*Primary Examiner* — Michael F Peffley
*Assistant Examiner* — Khadijeh A Vahdat

(57) ABSTRACT

A method includes providing a bipolar energy source, a monopolar energy source, a bipolar assembly, and a monopolar assembly. The method further includes moving the monopolar assembly to a retracted position. Moving the monopolar assembly to the retracted position couples the bipolar energy source to the bipolar assembly and decouples the monopolar energy source from the monopolar assembly. The method further includes moving the monopolar assembly to a deployed position. Moving the monopolar assembly to the deployed position decouples the bipolar energy source from the bipolar assembly and couples the monopolar energy source to the monopolar assembly.

20 Claims, 8 Drawing Sheets

Related U.S. Application Data

(60) Provisional application No. 61/873,230, filed on Sep. 3, 2013, provisional application No. 61/873,219, filed on Sep. 3, 2013.

(52) U.S. Cl.
CPC ............... *A61B 2018/0063* (2013.01); *A61B 2018/00083* (2013.01); *A61B 2018/00922* (2013.01); *A61B 2018/00946* (2013.01); *A61B 2018/00952* (2013.01); *A61B 2018/126* (2013.01); *A61B 2018/1253* (2013.01); *A61B 2018/1455* (2013.01); *A61B 2018/1475* (2013.01)

(58) Field of Classification Search
CPC .. A61B 2018/00083; A61B 2018/0063; A61B 2018/00922; A61B 2018/00946; A61B 2018/00952; A61B 2018/1253; A61B 2018/126; A61B 2018/1455; A61B 2018/1475
USPC ........................ 606/51–52, 169, 205–207
See application file for complete search history.

(56) References Cited

U.S. PATENT DOCUMENTS

| | | | |
|---|---|---|---|
| 5,324,254 A | 6/1994 | Phillips | |
| 5,401,274 A | 3/1995 | Kusunoki | |
| 5,445,638 A | 8/1995 | Rydell et al. | |
| 5,458,598 A | 10/1995 | Feinberg et al. | |
| 5,556,397 A | 9/1996 | Long et al. | |
| 5,735,873 A | 4/1998 | MacLean | |
| 5,792,164 A | 8/1998 | Lakatos et al. | |
| 5,893,863 A | 4/1999 | Yoon | |
| 5,919,202 A | 7/1999 | Yoon | |
| 5,928,159 A | 7/1999 | Eggers et al. | |
| 6,113,596 A | 9/2000 | Hooven et al. | |
| 6,156,009 A | 12/2000 | Grabek | |
| 6,190,386 B1 | 2/2001 | Rydell | |
| 6,270,497 B1 | 8/2001 | Sekino et al. | |
| 6,299,625 B1 | 10/2001 | Bacher | |
| 6,387,094 B1 | 5/2002 | Eitenmuller | |
| 6,551,313 B1 | 4/2003 | Levin | |
| 6,679,882 B1 | 1/2004 | Komerup | |
| 6,808,525 B2 | 10/2004 | Latterell et al. | |
| 6,942,662 B2 | 9/2005 | Goble et al. | |
| 7,033,356 B2 | 4/2006 | Latterell et al. | |
| 7,063,699 B2 | 6/2006 | Hess et al. | |
| 7,128,254 B2 | 10/2006 | Shelton, IV et al. | |
| 7,232,440 B2 | 6/2007 | Dumbauld et al. | |
| 7,367,976 B2 | 5/2008 | Lawes et al. | |
| 7,402,162 B2 | 7/2008 | Ouchi | |
| 7,442,194 B2 * | 10/2008 | Dumbauld ......... A61B 18/1445 606/41 |
| 7,445,621 B2 | 11/2008 | Dumbauld et al. | |
| 7,510,562 B2 | 3/2009 | Lindsay | |
| 7,588,570 B2 | 9/2009 | Wakikaido et al. | |
| 7,658,311 B2 | 2/2010 | Boudreaux | |
| 7,758,577 B2 | 7/2010 | Nobis et al. | |
| 7,815,636 B2 | 10/2010 | Ortiz | |
| 7,819,872 B2 | 10/2010 | Johnson et al. | |
| 8,257,352 B2 | 9/2012 | Lawes et al. | |
| 8,353,437 B2 | 1/2013 | Boudreaux | |
| 9,597,141 B2 | 3/2017 | Garrison et al. | |
| 2002/0049442 A1 | 4/2002 | Roberts et al. | |
| 2004/0236326 A1 | 11/2004 | Schulze et al. | |
| 2005/0113827 A1 | 5/2005 | Dumbauld et al. | |
| 2005/0187547 A1 | 8/2005 | Sugi | |
| 2008/0215050 A1 | 9/2008 | Bakos | |
| 2009/0125026 A1 | 5/2009 | Rioux et al. | |
| 2009/0125027 A1 | 5/2009 | Fischer | |
| 2009/0131974 A1 | 5/2009 | Pedersen et al. | |
| 2009/0254084 A1 | 10/2009 | Naito | |
| 2010/0185196 A1 | 7/2010 | Sakao et al. | |
| 2010/0185197 A1 | 7/2010 | Sakao et al. | |
| 2010/0292690 A1 | 11/2010 | Livneh | |
| 2011/0087218 A1 | 4/2011 | Boudreaux et al. | |
| 2011/0130757 A1 | 6/2011 | Horlle et al. | |
| 2011/0264093 A1 | 10/2011 | Schall | |
| 2012/0330351 A1 | 12/2012 | Friedman et al. | |
| 2013/0178845 A1 * | 7/2013 | Smith .................... A61B 18/18 606/33 |
| 2014/0276797 A1 | 9/2014 | Batchelor et al. | |

OTHER PUBLICATIONS

European examination report issued in corresponding EP application No. 14173014.1 dated Dec. 4, 2017, 5 pages.

* cited by examiner

SWITCH ASSEMBLIES FOR MULTI-FUNCTION SURGICAL INSTRUMENTS AND SURGICAL INSTRUMENTS INCORPORATING THE SAME

CROSS-REFERENCE TO RELATED APPLICATIONS

This application is a continuation application claiming the benefit of, and priority to, U.S. patent application Ser. No. 14/280,834, filed on May 19, 2014, now U.S. Pat. No. 9,597,141, which claims the benefit of, and priority to, U.S. Provisional Patent Application Nos. 61/873,219 and 61/873,230, both of which were filed on Sep. 3, 2013. This application is related to U.S. patent application Ser. No. 14/280,779, filed on May 19, 2014, now U.S. Pat. No. 9,713,492. The entire contents of each of the above applications are hereby incorporated herein by reference.

BACKGROUND

Technical Field

The present disclosure relates to surgical instruments and, more particularly, to multi-function surgical instruments including switch assemblies configured to switch between monopolar and bipolar modes of operation.

Background of Related Art

Bipolar surgical instruments, e.g., bipolar electrosurgical forceps, typically include two generally opposing electrodes charged to different electrical potentials for conducting energy therebetween and through tissue. Bipolar electrosurgical forceps utilize both mechanical clamping action and electrical energy to effect hemostasis by heating tissue and blood vessels to coagulate and/or cauterize tissue. Certain surgical procedures require more than simply cauterizing tissue and rely on the unique combination of clamping pressure, precise electrosurgical energy control and gap distance (i.e., distance between opposing jaw members when closed about tissue) to "seal" tissue.

Monopolar surgical instruments, on the other hand, include an active electrode, and are used in conjunction with a remote return electrode, e.g., a return pad, to apply energy to tissue. Monopolar instruments have the ability to rapidly move through tissue and dissect through narrow tissue planes.

In some surgical procedures, it may be beneficial to use both bipolar and monopolar instrumentation, e.g., procedures where it is necessary to dissect through one or more layers of tissue in order to reach underlying tissue(s) to be sealed. Further, it may be beneficial, particularly with respect to endoscopic surgical procedures, to provide a singe instrument incorporating both bipolar and monopolar features, thereby obviating the need to alternatingly remove and insert the bipolar and monopolar instruments in favor of one another.

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any or all of the other aspects described herein.

In accordance with aspects of the present disclosure, a method includes providing a bipolar energy source, a monopolar energy source, a bipolar assembly, and a monopolar assembly. The method further includes moving the monopolar assembly to a retracted position, and moving the monopolar assembly to a deployed position. Moving the monopolar assembly to the retracted position couples the bipolar energy source to the bipolar assembly and decouples the monopolar energy source from the monopolar assembly. Moving the monopolar assembly to the deployed position, on the other hand, decouples the bipolar energy source from the bipolar assembly and couples the monopolar energy source to the monopolar assembly.

In aspects, with the monopolar assembly disposed in the retracted position, the method further includes supplying bipolar energy from the bipolar energy source to the bipolar assembly for conducting bipolar energy through tissue to treat tissue.

In aspects, conducting bipolar energy through tissue to treat tissue includes conducting energy between first and second electrically-conductive plates of the bipolar assembly to seal tissue disposed therebetween.

In aspects, with the monopolar assembly disposed in the deployed position, the method further includes supplying monopolar energy from the monopolar energy source to the monopolar assembly for applying monopolar energy to tissue to treat tissue.

In aspects, applying monopolar energy to tissue to treat tissue includes applying energy from an energizable rod member of the monopolar assembly to tissue to dissect tissue adjacent the energizable rod member.

In aspects, the method further includes moving the monopolar assembly to an intermediate position, wherein moving the monopolar assembly to the intermediate position decouples the bipolar energy source from the bipolar assembly and decouples the monopolar energy source from the monopolar assembly.

In aspects, the intermediate position of the monopolar assembly is disposed between the retracted position and the deployed position such that the monopolar assembly is moved through the intermediate position upon movement of the monopolar assembly between the retracted position and the deployed position.

In aspects, the monopolar assembly includes a energizable portion and an insulative portion, and moving the monopolar assembly to the deployed position includes at least partially covering the bipolar assembly with the insulative portion and extending the energizable portion from the insulative portion.

Another method provided in accordance with the present disclosure includes providing first and second bipolar inputs coupled to a bipolar source of energy, first and second bipolar outputs coupled to first and second energizable members, a monopolar input coupled to a monopolar source of energy, and a monopolar output coupled to a third energizable member. The method further includes moving the third energizable member to a retracted position, and moving the third energizable member to a deployed position. Moving the third energizable member to the retracted position couples the first and second bipolar inputs to the first and second bipolar outputs, respectively, and decouples the monopolar input from the monopolar output. Moving the third energizable member to a deployed position, on the other hand, decouples the first and second bipolar inputs from the first and second bipolar outputs, respectively, and couples the monopolar input to the monopolar output.

In aspects, with the third energizable member disposed in the retracted position, the method further includes supplying bipolar energy from the bipolar energy source to the first and second energizable members for conducting bipolar energy through tissue to treat tissue.

In aspects, conducting bipolar energy through tissue to treat tissue includes conducting energy between the first and second energizable members to seal tissue disposed therebetween.

In aspects, with the third energizable member disposed in the deployed position, the method further includes supplying monopolar energy from the monopolar energy source to the third energizable member for applying monopolar energy to tissue to treat tissue.

In aspects, applying monopolar energy to tissue to treat tissue includes applying energy from the third energizable member of the monopolar assembly to tissue to dissect tissue adjacent the third energizable member.

In aspects, the method further includes moving the third energizable member to an intermediate position, wherein moving the third energizable member to the intermediate position decouples the first and second bipolar inputs from the first and second bipolar outputs, respectively, and decouples the monopolar input from the monopolar output.

In aspects, the intermediate position of the third energizable member is disposed between the retracted position and the deployed position such that the third energizable member is moved through the intermediate position upon movement of the third energizable member between the retracted position and the deployed position.

In aspects, the method further includes providing an insulative portion, wherein moving the third energizable member to the deployed position includes at least partially covering the first and second energizable members with the insulative portion and extending the third energizable member from the insulative portion.

BRIEF DESCRIPTION OF THE DRAWINGS

Various aspects of the present disclosure are described herein with reference to the drawings wherein like reference numerals identify similar or identical elements.

DETAILED DESCRIPTION

Figure 1:
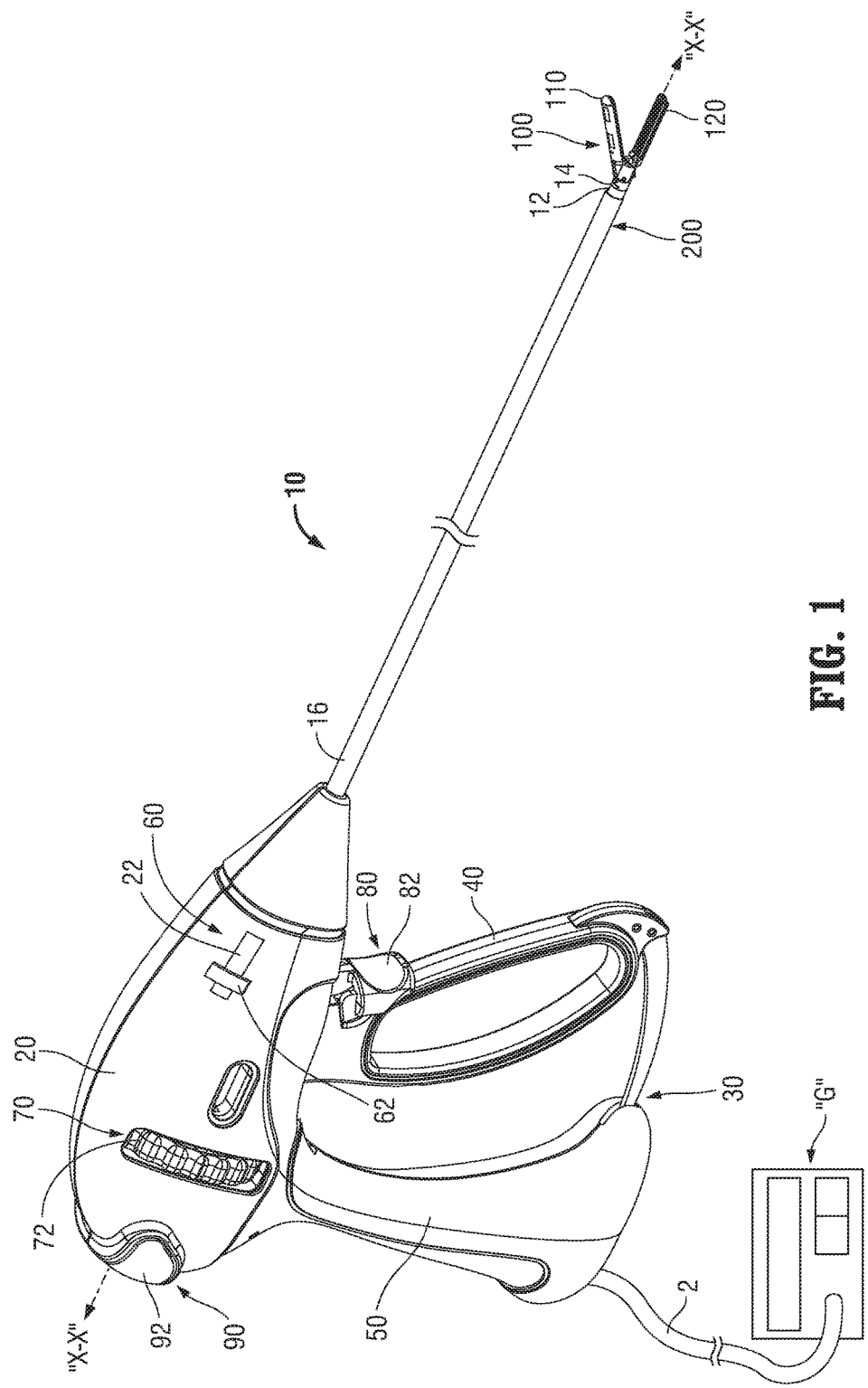
FIG. 1 is a front, perspective view of an endoscopic surgical forceps configured for use in accordance with the present disclosure.
Figure 2A:
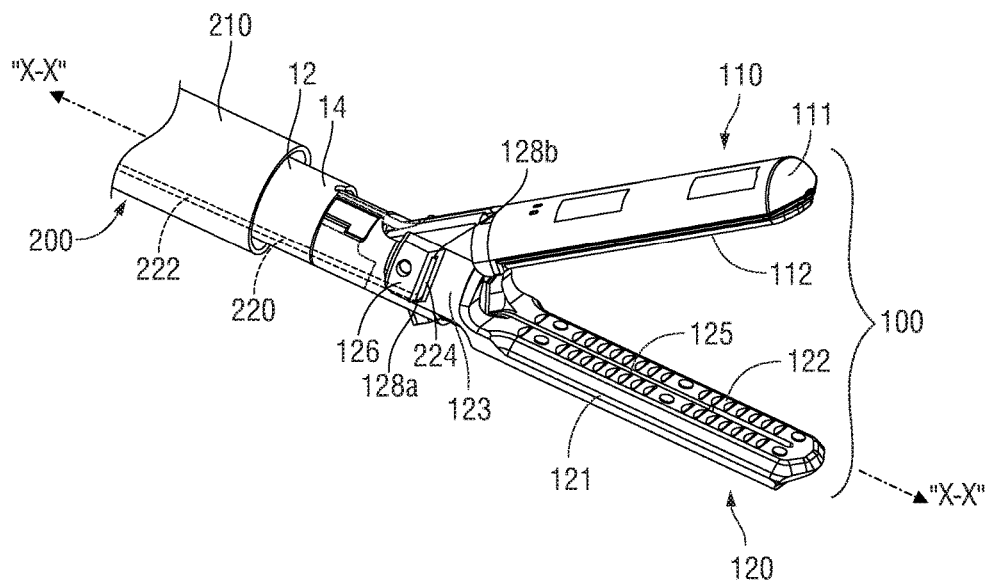
FIG. 2A is an enlarged, perspective partial-view of the end effector assembly of the forceps of FIG. 1, wherein the jaw members of the end effector assembly are disposed in a spaced-apart position and wherein the monopolar assembly is disposed in a retracted position.
Figure 2B:
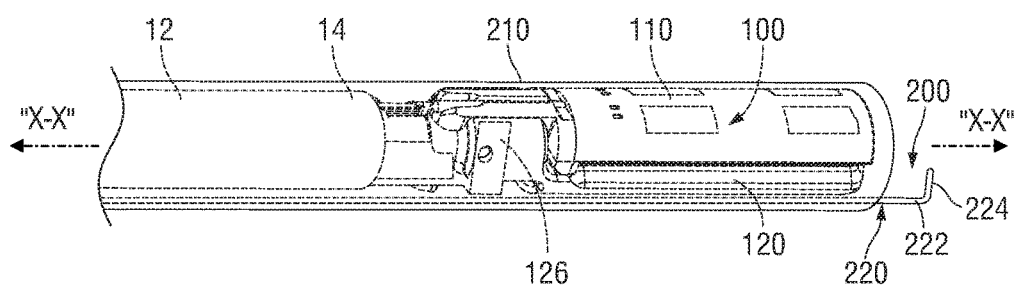
FIG. 2B is an enlarged, perspective partial-view of the end effector assembly of FIG. 2A, wherein the jaw members are disposed in the approximated position and wherein the monopolar assembly is disposed in a deployed position.
Figure 3:
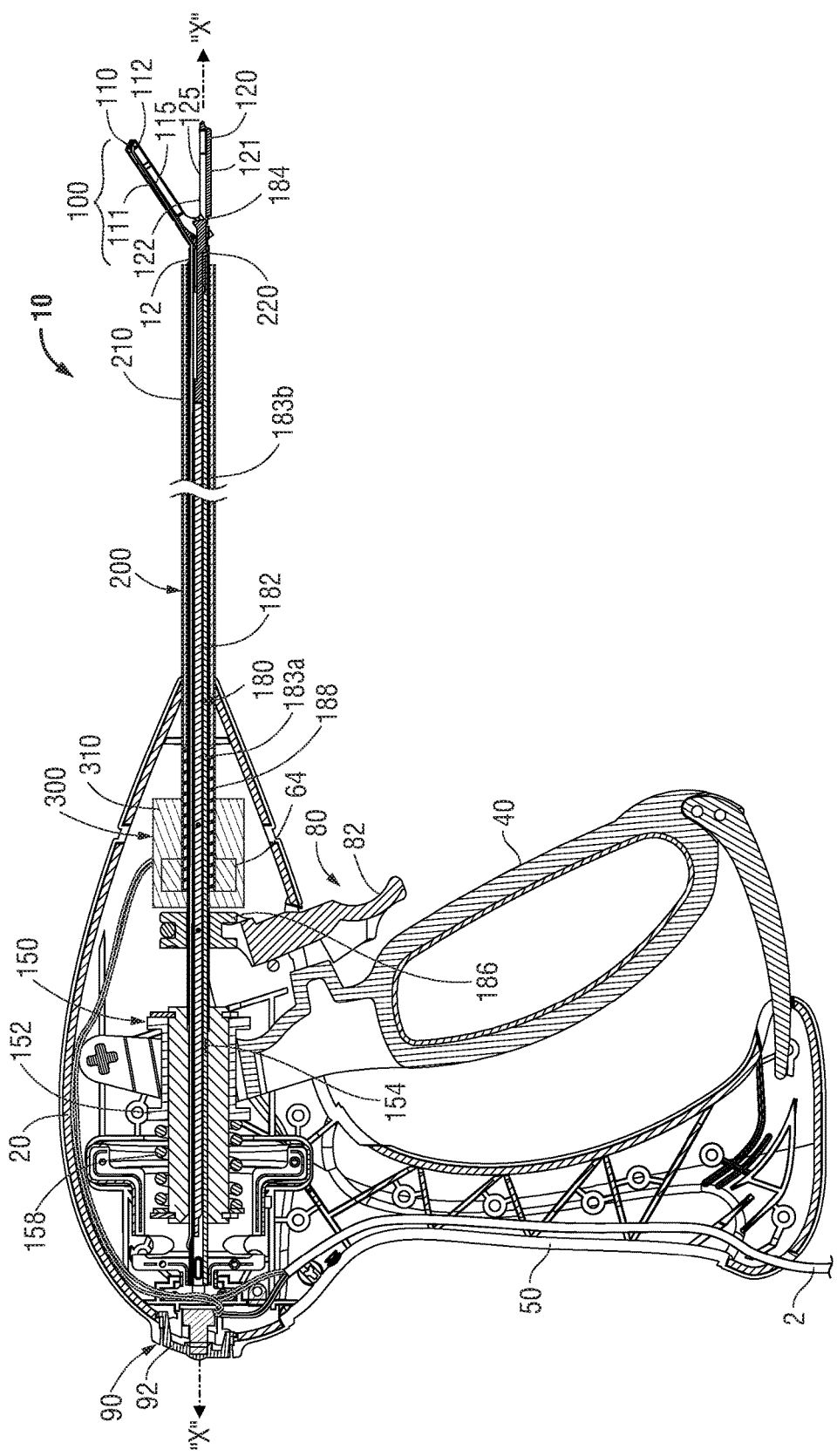
FIG. 3 is a longitudinal, cross-sectional view of the forceps of FIG. 1.

Referring to FIGS. 1-3, a forceps including features for operating in both a bipolar mode, e.g., for grasping and/or treating tissue, and a monopolar mode, e.g., for treating and/or dissecting tissue, is shown generally identified by reference numeral 10. Although shown as an endoscopic forceps 10, it is contemplated that forceps 10 also be configured for use in connection with traditional open surgical procedures. Further, although a surgical forceps is shown and described herein, it is also contemplated that the aspects and features of the present disclosure be provided for use in conjunction with any suitable multifunction surgical instrument, e.g., any suitable surgical instrument capable of operating in both a bipolar mode and a monopolar mode (or any two different modes). Obviously, different electrical and mechanical connections and considerations apply to each particular configuration; however, the aspects and features of the present disclosure remain generally consistent with respect to both open and endoscopic forceps as well as other suitable surgical instruments.

Continuing with reference to FIGS. 1-3, forceps 10 defines a longitudinal axis "X-X" and includes a housing 20 incorporating a handle assembly 30, a deployment assembly 60, a rotating assembly 70, a trigger assembly 80, an activation assembly 90, and a switch assembly 300 (FIG. 3). Forceps 10 also includes an end effector assembly 100 configured to grasp, treat, e.g., seal, and/or divide tissue; a shaft 12 having a distal end 14 configured to mechanically engage end effector assembly 100 and a proximal end 16 that mechanically engages housing 20; and a monopolar assembly 200 selectively deployable (see FIGS. 2A-2B) from shaft 12 about end effector assembly 100 for treating and/or dissecting tissue.

As best shown in FIG. 3, forceps 10 further includes an electrosurgical cable 2 that connects forceps 10 to a source of energy, e.g., a generator "G" (FIG. 1), although forceps 10 may alternatively be configured as a battery powered instrument including an on-board generator housed within or mounted on housing 20. Cable 2 houses a plurality of wires (see also FIGS. 5 and 6A-6B) that extend from cable 2 into housing 20 to electrically couple generator "G" (FIG. 1), activation assembly 90, and switch assembly 300 to one another. Switch assembly 300, as will be described in greater detail below, is transitionable between a first condition, corresponding to the bipolar mode of operation, wherein switch assembly 300 electrically couples generator "G" (FIG. 1) and activation assembly 90 to end effector assembly 100 for selectively supplying energy to end effector assembly 100 upon actuation of activation button 92 of activation assembly 90, and a second condition, corresponding to the monopolar mode of operation, wherein switch assembly 300 electrically couples generator "G" (FIG. 1) and activation assembly 90 to monopolar assembly 200 for selectively supplying energy to monopolar assembly 200 upon actuation of activation button 92 of activation assembly 90. In the first condition, monopolar assembly 200 is decoupled from generator "G" (FIG. 1) and activation assembly 90 while, in the second condition, end effector assembly 100 is decoupled from generator "G" (FIG. 1) and activation assembly 90. Alternatively, end effector assembly 100 and monopolar assembly 200 may have separate activation buttons, with the same effect of being coupled or decoupled depending on the condition of switch assembly 300.

With additional reference to FIGS. 1 and 2A-2B, end effector assembly 100 is shown attached at a distal end 14 of shaft 12 and includes a pair of opposing jaw members 110, 120. Each jaw member 110, 120 includes an electrically-insulative outer jaw housing 111, 121 and an electrically-conductive tissue sealing surface defined by an electrically-conductive plate 112, 122 disposed atop respective jaw housings 111, 121, although other configurations are also contemplated. Electrically-conductive plates 112, 122 of jaw members 110, 120, respectively, are electrically coupled to switch assembly 300 (FIG. 3) which, as mentioned above, electrically couples plates 112, 122 to generator "G" and activation assembly 90 when disposed in the first condition. As such, energy may be selectively supplied to plates 112, 122, e.g., via actuating activation button 92 of activation assembly 90, for conduction therebetween and through tissue grasped between jaw members 110, 120 to treat, e.g., seal, tissue, when switch assembly 300 (FIG. 3) is disposed in the first condition. End effector assembly 100 defines a bipolar configuration wherein plate 112 is charged to a first electrical potential and plate 122 is charged to a second, different electrical potential to create an electrical potential gradient therebetween for conducting energy between plates 112, 122 and through tissue grasped therebetween for treating e.g., sealing, tissue.

End effector assembly 100 is configured as a unilateral assembly, i.e., where jaw member 120 is fixed relative to shaft 12 and jaw member 110 is movable relative to shaft 12 and fixed jaw member 120. However, end effector assembly 100 may alternatively be configured as a bilateral assembly, i.e., where both jaw member 110 and jaw member 120 are movable relative to one another and to shaft 12. In some embodiments (as shown), a knife assembly 180 is disposed within shaft 12 and a knife channel 115, 125 is defined within one or both jaw members 110, 120 to permit reciprocation of a knife 184 therethrough, e.g., via actuation of a trigger 82 of trigger assembly 80. Alternatively, an electrical-cutting electrode, static or dynamic, may be provided for cutting tissue grasped between jaw members 110, 120.

Continuing with reference to FIGS. 1-3, one of the jaw members 110, 120 of end effector assembly 100, e.g., jaw member 120, is configured to house energizable rod member 220 of monopolar assembly 200. More specifically, the proximal flange portion of one of the jaw members, e.g., proximal flange portion 123 of jaw member 120, includes an extension portion 126 having a lumen 128a and recess 128b defined therein. Lumen 128a extends through extension portion 126 into communication with recess 128b, which is defined within a distally-facing surface of proximal flange portion 123 of jaw member 120. This configuration of proximal flange portion 123 of jaw member 120 permits body 222 of energizable rod member 220 of monopolar assembly 200 to extend through proximal flange portion 123 of jaw member 120, e.g., through lumen 128a, while also permitting distal tip 224 of rod member 220 of monopolar assembly 200 to be received within recess 128b of proximal flange portion 123 when monopolar assembly 200 is disposed in the retracted position, thereby helping to protect surrounding tissue. The entire proximal flange portion 123 of jaw member 120 or simply extension portion 126 thereof may be formed from an insulative material or may be coated with an insulative material to facilitate the insulation of distal tip 224 of energizable rod member 220 from electrically-conductive plates 112, 122 of jaw members 110, 120, when monopolar assembly 200 is disposed in the retracted position. Monopolar assembly 200 will be described in greater detail hereinbelow.

Figure 4A:
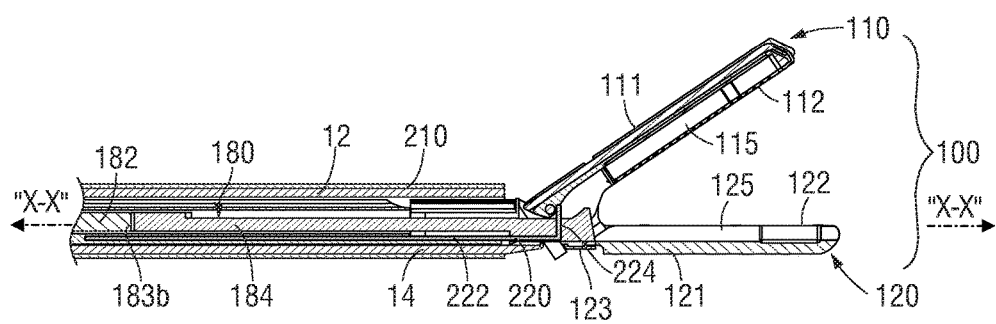
FIG. 4A is a longitudinal, cross-sectional view of the end effector assembly of FIG. 2A, wherein the jaw members are disposed in the spaced-apart position.

Referring to FIGS. 1 and 3, handle assembly 30 includes a fixed handle 50 and a movable handle 40. Fixed handle 50 is integrally associated with housing 20 and movable handle 40 is moveable relative to fixed handle 50. Movable handle 40 is ultimately connected to a drive assembly 150 that, together, mechanically cooperate to impart movement of jaw members 110 and 120 between a spaced-apart position (FIG. 4A) and an approximated position (FIG. 4B) to grasp tissue between plates 112 and 122 of jaw members 110, 120, respectively. More specifically, as shown in FIG. 3, drive assembly 150 includes a mandrel 152 disposed about a drive sleeve 154. Mandrel 152 operably couples movable handle 40 to drive sleeve 154. Drive sleeve 154, in turn, is operably coupled to jaw member 110 (and/or jaw member 120) such that longitudinal actuation of movable handle 40 translates drive sleeve 154 relative to and through shaft 12 to pivot jaw member 110 relative to jaw member 120 between the spaced-apart and approximated positions for grasping tissue therebetween. As shown in FIG. 1, movable handle 40 is initially spaced-apart from fixed handle 50 and, correspondingly, jaw members 110, 120 are disposed in the spaced-apart position. Movable handle 40 is movable from this initial position to a depressed position to urge drive sleeve 154 proximally through shaft 12 and relative to end effector assembly 100 to move jaw members 110, 120 to the approximated position for grasping tissue therebetween (see FIG. 4B). Upon release of movable handle 40, drive sleeve 154 is returned distally under the bias of biasing member 158 to return jaw members 110, 120 to the spaced-apart position. Rotation wheel 72 of rotating assembly 70 is rotatable in either direction about longitudinal axis "X-X" to rotate end effector assembly 100 about longitudinal axis "X-X."

Figure 4B:
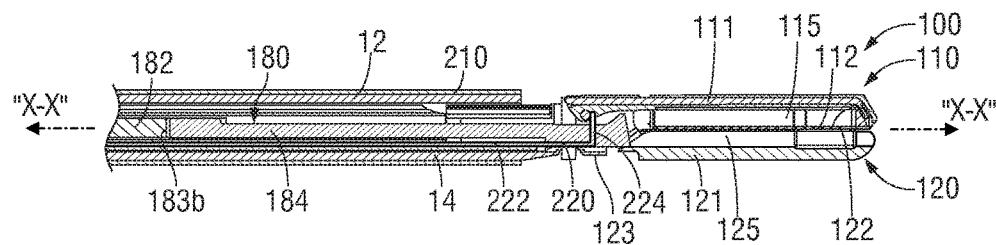
FIG. 4B is a longitudinal, cross-sectional view of the end effector assembly of FIG. 2A, wherein the jaw members are disposed in the approximated position.

Referring to FIGS. 1, 3, and 4A-4C, trigger assembly 80 is coupled to knife assembly 180 such that trigger 82 is selectively actuatable from an un-actuated position to an actuated position to advance knife 184 from a storage position (FIG. 4B), wherein knife 184 is disposed proximally relative to jaw members 110, 120, to an extended position, wherein knife 184 extends between jaw members 110, 120 and through knife channels 115, 125, respectively (FIG. 4C), to cut tissue grasped between jaw members 110, 120. Knife assembly 180 includes a knife drive shaft 182 defining proximal and distal ends 183a, 183b, respectively. A mandrel 186 operably coupled to trigger 82 is disposed about knife drive shaft 182 towards proximal end 183a thereof such that knife 184 is selectively advanced between jaw members 110, 120 upon actuation of trigger 82. A biasing member 188 biases knife assembly 180 towards the storage position (FIG. 4B).

With reference to FIGS. 2A-2B, monopolar assembly 200 includes an insulative sleeve 210 and an energizable rod member 220. Insulative sleeve 210 is slidably disposed about shaft 12 and is configured for translation about and relative to shaft 12 and end effector assembly 100 between a retracted position (FIGS. 2A and 4A-4C), where insulative sleeve 210 is disposed proximally of end effector assembly 100, and a deployed position (FIGS. 2B and 4D), wherein insulative sleeve 210 is disposed about end effector assembly 100 so as to electrically insulate electrically-conductive plates 112, 122 of jaw members 110, 120, respectively, from the surroundings of insulative sleeve 210. Monopolar assembly 200 may be biased towards the retracted position and/or may further include a locking assembly (not shown) for selectively locking monopolar assembly 200 in the retracted and/or the deployed position.

Energizable rod member 220 of monopolar assembly 200 includes an elongated body 222 and a distal tip 224 that may be oriented relative to elongated body 222 to define a hook-shaped or other suitable configuration. Energizable rod member 220 is movable between a retracted position, wherein energizable rod member 220 is disposed within recess 128b of extension portion 126 of proximal flange portion 123 of jaw member 120 (FIG. 2A), and a deployed position, wherein energizable rod member 220 extends distally from end effector assembly 100 (FIG. 2B). Energizable rod member 220 is electrically coupled to switch assembly 300 (FIG. 3) such that, in the second condition of switch assembly 300, switch assembly 300 electrically couples generator "G" (FIG. 1) and activation assembly 90 to energizable rod member 220 of monopolar assembly 200 for selectively supplying energy to energizable rod member 220 upon actuation of activation button 92 of activation assembly 90. As an alternative to sharing activation assembly 90, it is also contemplated that two separate activation assemblies be provided for activating end effector assembly 100 and monopolar assembly 200.

With additional reference to FIGS. 1 and 3, the proximal end of insulative sleeve 210 of monopolar assembly 200, which extends into housing 20, is coupled to deployment assembly 60, e.g., base member 64 of deployment assembly 60 (see FIGS. 6A-6B), for allowing selective deployment and retraction of insulative sleeve 210. A pair of sliders 62 of deployment assembly 60 extend through slots 22 defined on either side of housing 20 to facilitate selective translation of sliders 62 along slots 22, although only one slider 62 need be provided, on one side of housing 20. More specifically, either or both sliders 62 are translatable between a first, proximal position and a second, distal position for translating insulative sleeve 210 relative to shaft 12 and end effector assembly 100 between the retracted position (FIGS. 4A-4C) and the extended position (FIG. 4D). As an alternative to slider 62, other suitable deployment assemblies, e.g., levers, triggers, switches, etc., are also contemplated. Energizable rod member 220 is likewise coupled to deployment assembly 60, e.g., base member 64 (see FIGS. 6A-6B), such that translation of sliders 62 between the first and second positions translates energizable rod member 220 between the retracted and deployed positions concurrently or near concurrently with the translation of insulative sleeve 210 between the retracted and deployed positions. As such, the respective retracted and deployed positions of monopolar assembly 200 correspond to the configurations wherein both insulative sleeve 210 and energizable rod member 220 are retracted and deployed, respectively. As an alternative to coupling energizable rod member 220 directly to deployment assembly 60, energizable rod member 220 may be coupled to insulative sleeve 210 for establishing concurrent or near concurrent movement of energizable rod member 220 and insulative sleeve 210 between the retracted and deployed positions.

Figure 5:
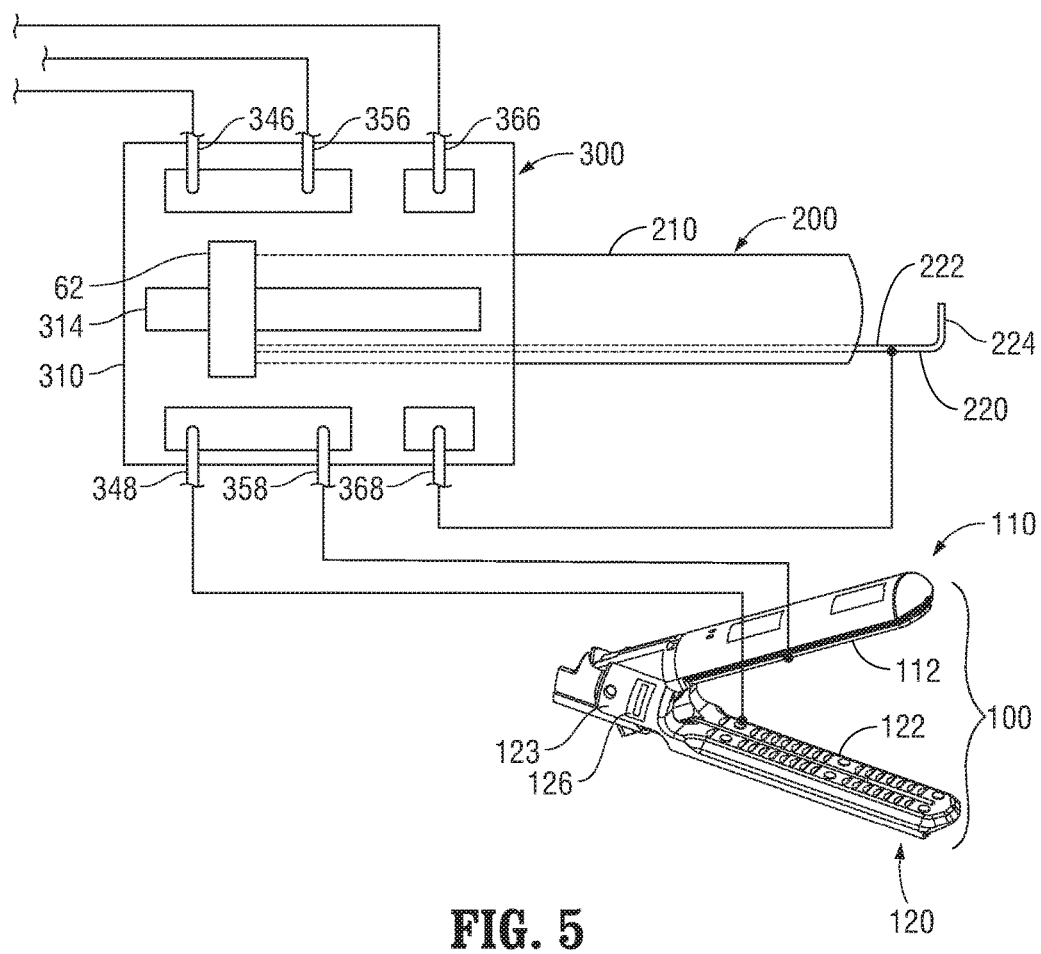
FIG. 5 is a schematic illustration of a switch assembly provided in accordance with the present disclosure and configured for selectively providing bipolar energy to the jaw members in a first condition and monopolar energy to the monopolar assembly in a second condition.
Figure 6A:
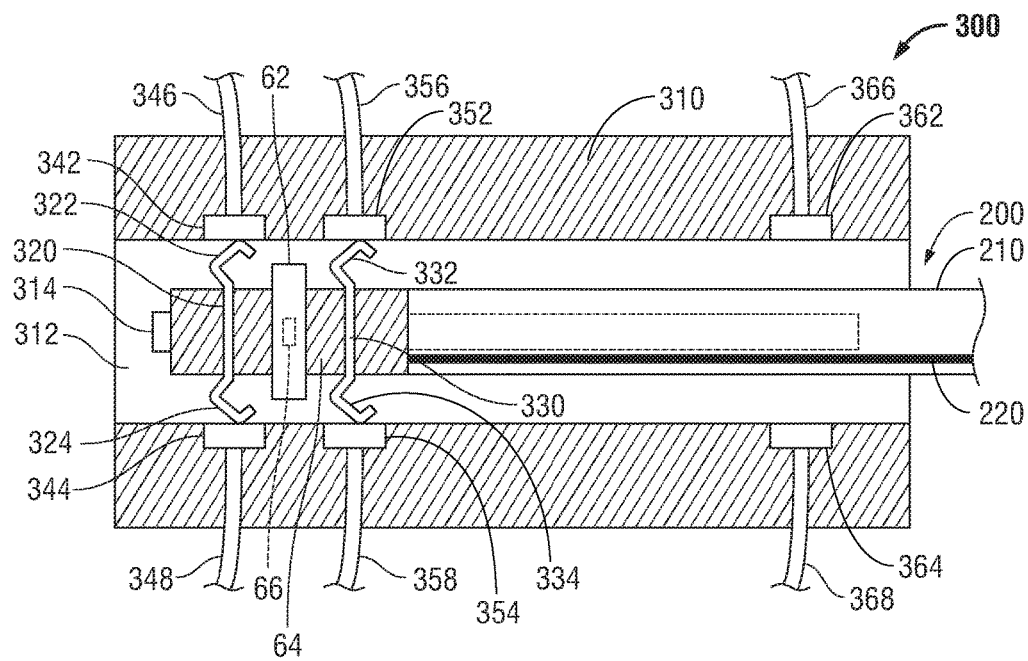
FIG. 6A is a cross-sectional view of the switch assembly of FIG. 5, wherein the switch assembly is disposed in the first condition.
Figure 6B:
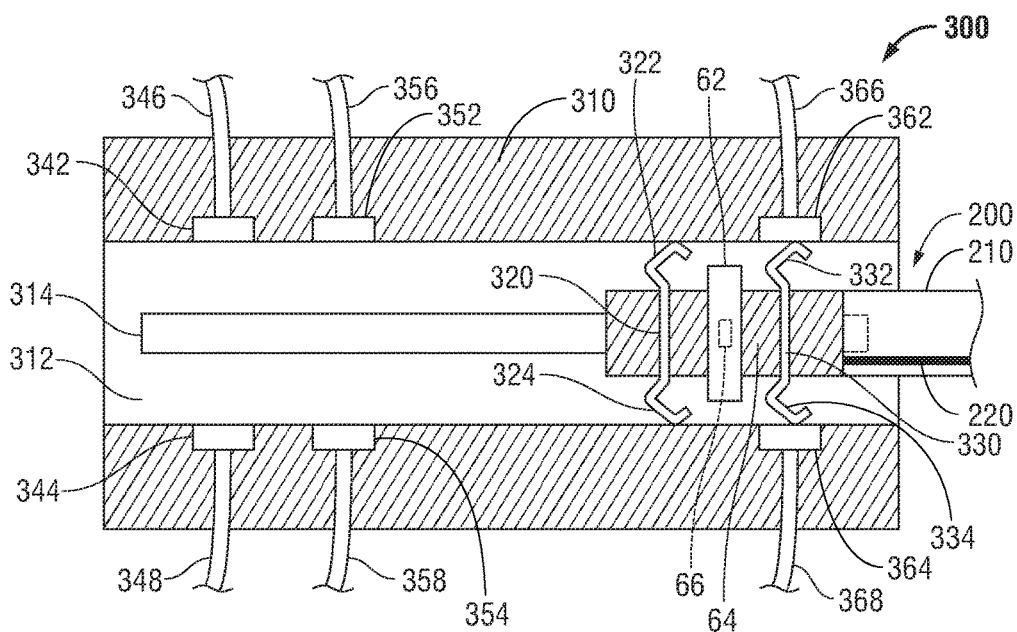
FIG. 6B is a cross-sectional view of the switch assembly of FIG. 5, wherein the switch assembly is disposed in the second condition.

Turning now to FIGS. 5 and 6A-6B, in conjunction with FIGS. 1-3, switch assembly 300 is described. Switch assembly 300, as noted above, is transitionable between a first condition, corresponding to the bipolar mode of operation, wherein generator "G" and activation assembly 90 are electrically coupled to electrically-conductive plates 112, 122 of jaw members 110, 120 of end effector assembly 100 and a second condition, corresponding to the monopolar mode of operation, wherein generator "G" and activation assembly 90 are electrically coupled to energizable rod member 220 of monopolar assembly 200. More specifically, upon translation of sliders 62 between the first and second positions, switch assembly 300 is transitioned between the first and second conditions. In other words, when monopolar assembly 200 is disposed in the retracted position, electrically-conductive plates 112, 122 are electrically coupled to generator "G" and activation assembly 90. Upon deployment of monopolar assembly 200, energizable rod member 220 is electrically coupled to generator "G" and activation assembly 90. In addition to selectively coupling end effector assembly 100 or monopolar assembly 200 to generator "G" and activation assembly 90, switch assembly 300 further decouples the other of the end effector assembly 100 or monopolar assembly 200 from generator "G" and activation assembly 90.

Referring in particular to FIGS. 5 and 6A-6B, switch assembly 300 includes a switch housing 310 mounted within housing 20 of forceps 10 (see FIG. 3). Switch housing 310 is formed at least partially from an insulative material and defines an internal passageway 312 configured to slidably receive the proximal end of insulative sleeve 210, energizable rod member 220, and drive sleeve 154 of drive assembly 150 (FIG. 3; drive sleeve 154 is not shown in FIGS. 5 and 6A-6B for simplicity purposes). As an alternative to passageway 312 receiving sleeve 210, switch assembly 300 may be spaced-from sleeve 210 and coupled thereto via one or more linkages (not shown).

Base member 64 of deployment assembly 60 is slidably disposed within internal passageway 312 of housing 310 and engages the proximal end of insulative sleeve 210 and the proximal end of energizable rod member 220, as mentioned above. A pair of opposed posts 66 extend from either side of base member 64 through opposed slots 314 defined within housing 310. Posts 66 extend through slots 314 of switch housing 310 and slots 22 defined within housing 20 of forceps 10 to engage sliders 62 of deployment assembly 60 such that translation of either slider 62 effects translation of base member 64 through internal passageway 312 of switch housing 310 and, thus, translation of insulative sleeve 210 and energizable rod member 220 between the retracted and deployed positions.

Base member 64 further includes a pair of spaced-apart electrically-conductive contact arms 320, 330 engaged thereto and extending therefrom. Contact arms 320, 330 are electrically insulated from one another via base member 64, which is made at least partially from an insulative material. Each contact arm 320, 330 extends from either side of base member 64 to define two pairs of opposed contact members 322, 324 and 332, 334. Contact members 322, 324 and 332, 334 each define a pre-bent configuration and are resiliently flexible inwardly towards base member 63. Each contact arm 320, 330 defines a total length greater than the width of passageway 312 of housing 310 such that contact members 322, 324, 332, 334 are biased into contact with the internal surface of housing 310 that defines passageway 312.

Housing 310 of switch assembly 300 further includes three pairs of opposed electrically-conductive contact plates 342, 344; 352, 354; and 362, 364. First and second pairs of contact plates 342, 344 and 352, 354 are disposed towards the proximal end of housing 310, while the third pair of contact plates 362, 364 is disposed towards the distal end of housing 310. Plates 342, 344; 352, 354; and 362, 364 are embedded within the internal surface of housing 310 that defines passageway 312 and are exposed to the interior of passageway 312. Accordingly, as will be described in greater detail below, base member 64 is selectively slidable through passageway 312 of housing 310 to orient contact arms 320, 330 between the desired pairs of plates 342, 344; 352, 354; and 362, 364 such that contact arms 320, 330 are biased into contact with the corresponding pairs of plates 342, 344; 352, 354; and 362, 364 to electrically couple the opposed plates 342, 344; 352, 354; and 362, 364 to one another via the contact arm 320, 330 extending therebetween.

Continuing with reference to FIGS. 5 and 6A-6B, in conjunction with FIGS. 1-3, each contact plate 342, 344, 352, 354, 362, 364 includes a wire (or wires) 346, 348, 356, 358, 366, 368, respectively, electrically coupled thereto and extending therefrom. First wire 346 is coupled to contact plate 342 and extends through switch housing 310, housing 20 of forceps 10, and cable 2, ultimately coupling to a positive bipolar terminal of generator "G." As mentioned above, first wire 346 may additionally be coupled to activation assembly 90, or activation assembly 90 may be coupled between generator "G" and first wire 346. Second wire 348 is coupled to contact plate 344, which opposes contact plate 342. Second wire 348 extends from switch housing 310 and through shaft 12, ultimately coupling to the positive electrically-conductive plate of end effector assembly 100, e.g., plate 122 of jaw member 120. As such, upon electrical coupling of first and second plates 342, 344 of switch assembly 300 to one another, e.g., via contact members 322, 324 of contact arm 320 when base member 64 is disposed in the first position, energy may be transmitted, e.g., upon actuation of activation assembly 90, from generator "G," through switch assembly 300, to electrically-conductive plate 122 of jaw member 120 for charging jaw member 120 to a first electrical potential.

Third wire 356 is similar to first wire 346 except that third wire 356 couples contact plate 352 to a negative bipolar terminal of generator "G" and/or activation assembly 90. Fourth wire 358 is similar to second wire 348 except that fourth wire 358 couples contact plate 354, which opposes contact plate 352, to the negative electrically-conductive plate of end effector assembly 100, e.g., plate 112 of jaw member 110 (although the polarity of plates 112, 122 may be reversed). As such, upon electrical coupling of plates 352, 354 of switch assembly 300 to one another, e.g., via contact members 332, 334 of contact arm 330 when base member 54 is disposed in the first position, energy may be transmitted from generator "G," through switch assembly 300, to electrically-conductive plate 112 of jaw member 110 for charging jaw member 110 to a second, different electrical potential.

Fifth wire 366 is coupled to contact plate 362 and extends through switch housing 310, housing 20 of forceps 10, and cable 2, ultimately coupling to an active monopolar terminal of generator "G," e.g., via or in addition to coupling to activation assembly 90. In use, the return pad (not shown) is coupled to the return monopolar terminal of generator "G." Sixth wire 368 is coupled to contact plate 264, which opposes contact plate 362, and extends though switch housing 310, ultimately coupling to energizable rod member 220 of monopolar assembly 200 such that, upon electrical coupling of plates 362, 364 to one another, e.g., via contact members 332, 334 of contact arm 330 when base member 64 is disposed in the second position, energy may be transmitted from generator "G" to energizable rod member 220.

Referring to FIGS. 1-6B, the use and operation of forceps 10 in both the bipolar mode, e.g., for grasping and treating and/or cutting grasped tissue, and the monopolar mode, e.g., for electrical/electromechanical tissue treatment, is described.

In order to use forceps 10 in the bipolar mode, either or both sliders 62 of deployment assembly 60 are moved to the proximal position (see FIG. 1). In this position, monopolar assembly 200 is disposed in its retracted position, as shown in FIGS. 2A and 4A-4C. Further, as shown in FIG. 5A, in the proximal position of slider 62, switch assembly 300 is disposed in the first condition, wherein base member 64 is positioned such that contact members 322, 324 of contact arm 320 are biased into contact with opposed plates 342, 344 to electrically couple generator "G" and activation assembly 90 to electrically-conductive plate 122 of jaw member 120 (see FIG. 5) and such that contact members 332, 334 of contact arm 330 are biased into contact with opposed plates 352, 354 to electrically couple generator "G" and activation assembly 90 to electrically-conductive plate 112 of jaw member 110 (see FIG. 5).

With forceps 10 in the bipolar mode of operation and with jaw members 110, 120 disposed in the spaced-apart position (FIG. 4A), end effector assembly 100 may be maneuvered into position such that tissue to be grasped, treated, e.g., sealed, and/or cut, is disposed between jaw members 110, 120. In particular, rotation wheel 72 may be manipulated to rotate jaw members 110, 120 to a desired orientation to receive tissue therebetween. Next, movable handle 40 is depressed or pulled proximally relative to fixed handle 50 such that jaw member 110 is pivoted relative to jaw member 120 from the spaced-apart position to the approximated position to grasp tissue therebetween, as shown in FIG. 4B. In this approximated position, energy may be supplied, e.g., via actuation of activation button 92 of activation assembly 90, to electrically-conductive plates 112, 122 of jaw members 110, 120 for conduction through tissue grasped therebetween to treat tissue, e.g., to effect a tissue seal.

Figure 4C:
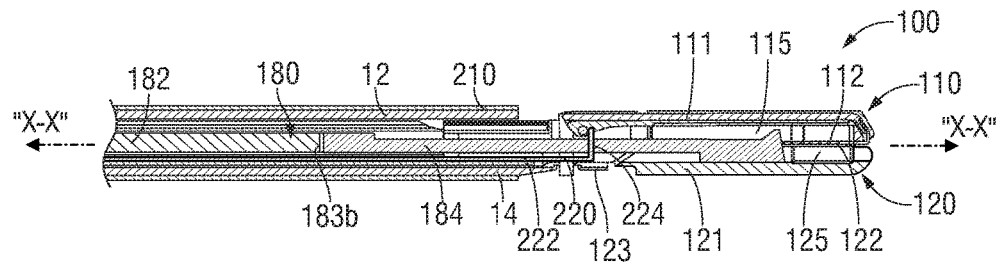
FIG. 4C is a longitudinal, cross-sectional view of the end effector assembly of FIG. 2A, wherein the jaw members are disposed in the approximated position and wherein the knife assembly is disposed in an extended position.
Figure 4D:
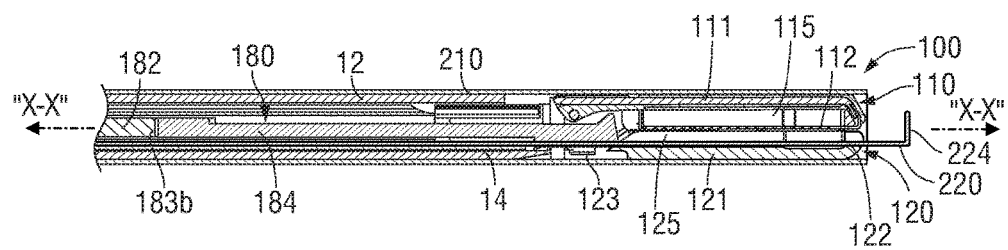
FIG. 4D is a longitudinal, cross-sectional view of the end effector assembly of FIG. 2A, wherein the monopolar assembly is disposed in the deployed position.

As shown in FIG. 4C, in conjunction with FIGS. 1 and 3, once tissue treatment is complete (or to cut untreated tissue), knife 184 of knife assembly 180 may be extended from within shaft 12 to between jaw members 110, 120, e.g., via actuation of trigger 82 of trigger assembly 80, to cut tissue grasped therebetween. More specifically, upon actuation of trigger 82, knife 184 is advanced at least partially through knife channels 115, 125 of jaw members 110, 120, respectively, to cut tissue grasped between jaw members 110, 120. Thereafter, knife 184 may be returned to within shaft 12 and jaw members 110, 120 may be moved back to the spaced-apart position (FIG. 4A) to release the treated and/or divided tissue.

With respect to operation of forceps 10 in the monopolar mode, movable handle 40 is first depressed relative to fixed handle 50 to pivot jaw members 110, 120 from the spaced-apart position to the approximated position. In some embodiments, this initial approximation of jaw members 110, 120 is not necessary, as deployment of monopolar assembly 200 may directly or indirectly effect approximation of jaw members 110, 120. Alternatively, where sleeve 210 allows (or is omitted), jaw members 110, 120 may remain in the open position during operation in the monopolar mode.

Once jaw members 110, 120 are disposed in the approximated position (if needed), monopolar assembly 200 is translated from the retracted position (FIGS. 2A and 4B) to the deployed position (FIGS. 2B and 4D) via movement of either or both sliders 62 from the proximal position to the distal position. More specifically, as slider(s) 62 are translated distally, base member 64 is translated distally though switch housing 310 to thereby translate insulative sleeve 210 distally over end effector assembly 100 and to translate energizable rod member 220 distally such that distal tip 224 of energizable rod member 220 extends distally from both end effector assembly 100 and insulative sleeve 210. In addition to mechanically deploying monopolar assembly 200, and concurrently or near-concurrently therewith, translation of slider(s) 62 from the proximal position to the distal position also transitions switch assembly 300 from the first condition to the second condition. More specifically, distal translation of slider(s) 62 translate base member 64 distally such that contact arm 330 is moved from between plates 352, 354 to between plates 362, 364, such that contact arm 320 is displaced from contact with plates 342, 344 (see FIG. 6B). As such, electrically-conductive plates 112, 122 of jaw members 110, 120 are no longer coupled to activation assembly 90 or generator "G" but, rather, activation assembly 90 and generator "G" are coupled to energizable rod member 220 of monopolar assembly 200.

As can be appreciated, when switch assembly 300 is disposed in an intermediate condition, e.g., between the first and second conditions, neither end effector assembly 100 nor monopolar assembly 200 is coupled to generator "G" and activation assembly 90. Such a configuration provides a safety feature for preventing use when monopolar assembly 200 is not fully disposed in either the retracted or deployed position.

With monopolar assembly 200 fully deployed, as shown in FIGS. 2B and 4D, activation button 92 may be actuated to supply energy to distal tip 224 of energizable rod member 220 for treating, e.g., electrically or electromechanically dissecting, tissue. Energy is returned to generator "G" via a remotely positioned return pad (not shown). During application of energy to distal tip 224 of energizable rod member 220, forceps 10 may be moved and/or manipulated relative to tissue to facilitate electromechanical treatment of tissue. Alternatively or additionally, forceps 10 may be moved or manipulated relative to tissue to facilitate mechanical tissue dissection, e.g., scoring tissue planes, with distal tip 224 in the absence of energy being applied to distal tip 224. During monopolar operation, with end effector assembly 100 decoupled from generator "G," both direct and indirect capacitive coupling between energizable rod member 220 and end effector assembly 100 are inhibited, thus inhibiting the occurrence of un-intended tissue effects as a result of capacitive coupling.

At the completion of tissue treatment, e.g., dissection, in the monopolar mode, monopolar assembly 200 may be returned to the retracted position (FIGS. 4A-4C), e.g., via moving either or both sliders 62 back to the proximal position. With monopolar assembly 200 once again disposed in the retracted position, jaw members 110, 120 of end effector assembly 100 may one again be manipulated to grasp, treat, and/or cut tissue, as described above, in the bipolar mode.

Figure 7:
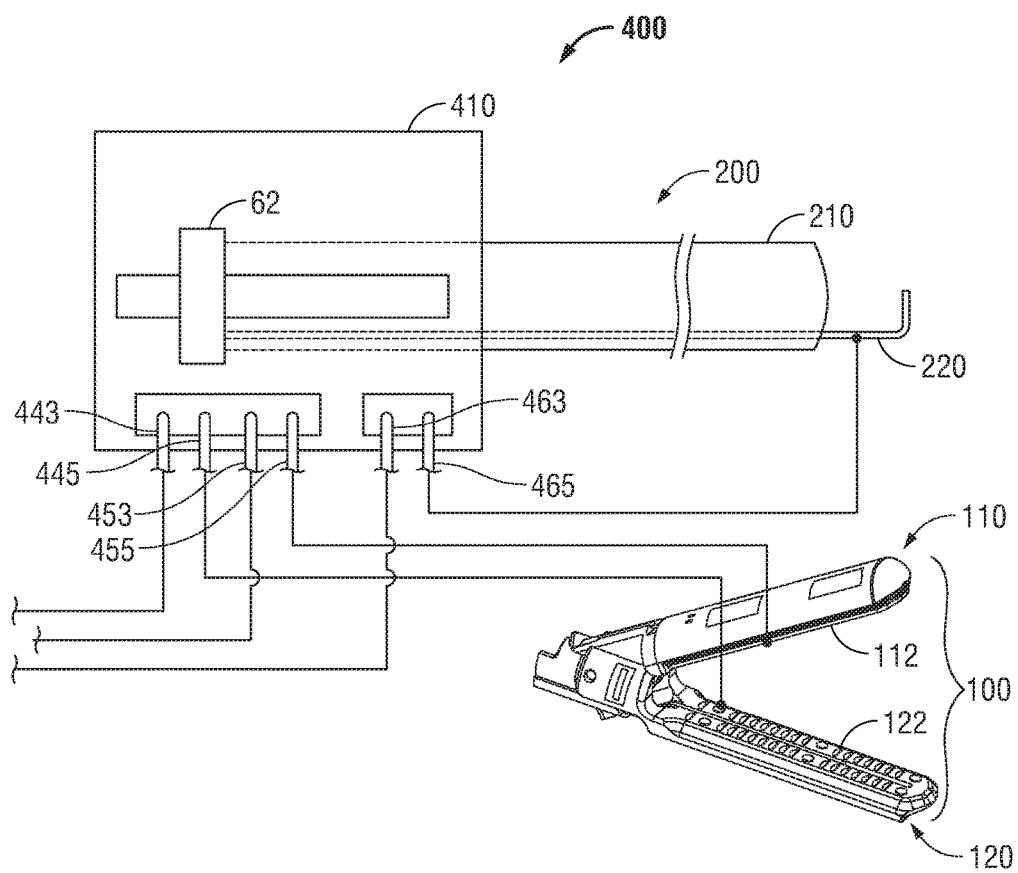
FIG. 7 is a schematic illustration of another switch assembly provided in accordance with the present disclosure and configured for selectively providing bipolar energy to the jaw members in a first condition and monopolar energy to the monopolar assembly in a second condition.
Figure 8A:
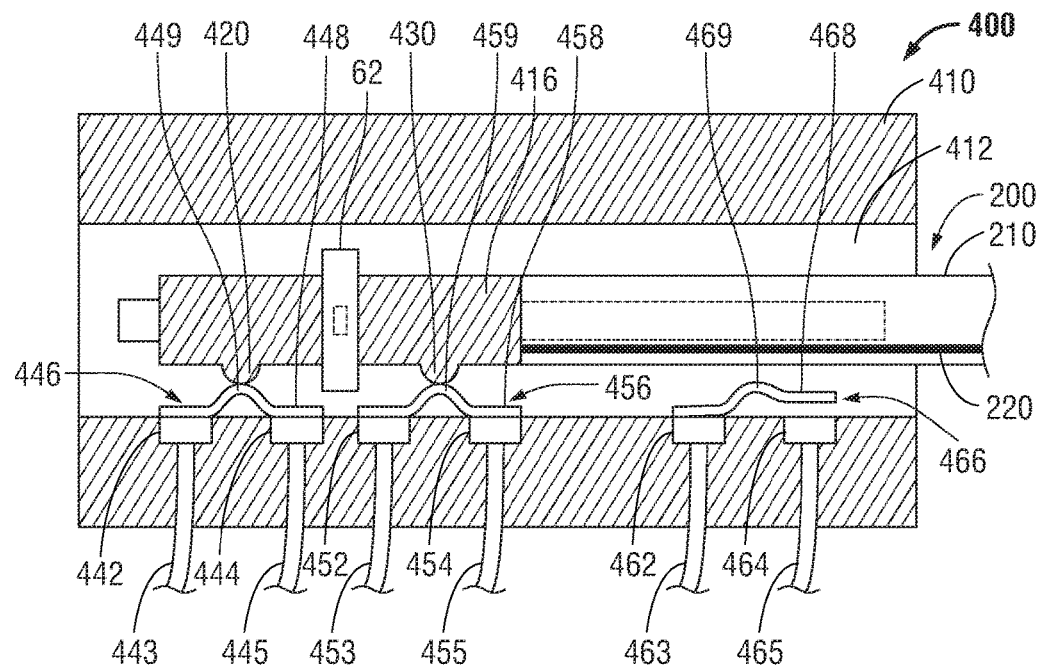
FIG. 8A is a cross-sectional view of the switch assembly of FIG. 7, wherein the switch assembly is disposed in the first condition.
Figure 8B:
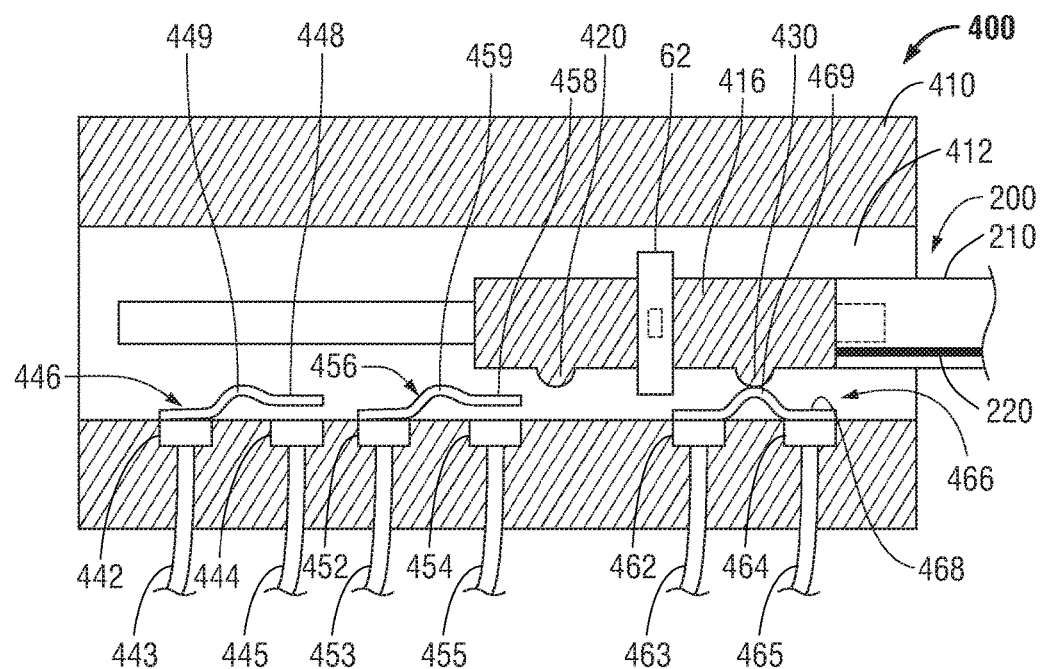
FIG. 8B is a cross-sectional view of the switch assembly of FIG. 7, wherein the switch assembly is disposed in the second condition.

Turning now to FIGS. 7 and 8A-8B, in conjunction with FIGS. 1-3, another embodiment of a switch assembly 400 configured for use with forceps 10 or any other suitable multi-function surgical instrument is described. Switch assembly 400, similar to switch assembly 300 (FIGS. 5 and 6A-6B), is transitionable between a first condition, corresponding to the bipolar mode of operation, wherein switch assembly 400 electrically couples generator "G" and activation assembly 90 to electrically-conductive plates 112, 122 of jaw members 110, 120 of end effector assembly 100 and a second condition, corresponding to the monopolar mode of operation, wherein switch assembly 400 electrically couples generator "G" and activation assembly 90 to energizable rod member 220 of monopolar assembly 200. Except where explicitly contradicted below, switch assembly 400 may include any or all of the features of switch assembly 300 (FIGS. 5 and 6A-6B), and vice versa. Further, similarities between switch assembly 400 and switch assembly 300 (FIGS. 5 and 6A-6B) may only be summarily described or omitted entirely for purposes of brevity.

Switch assembly 400 includes a switch housing 410 configured to be mounted within housing 20 of forceps 10 (see FIG. 1). Switch housing 410 defines an internal passageway 412. A base member 416 is slidably disposed within internal passageway 412, engaged to sliders 62 (FIG. 1), and engaged to the proximal end of insulative sleeve 210 and the proximal end of energizable rod member 220, similarly as detailed above with respect to switch assembly 300 (FIGS. 5 and 6A-6B). Base member 416 further includes a pair of spaced-apart protrusions 420, 430 protruding from a surface thereof.

Housing 410 of switch assembly 400 further includes three pairs of adjacent electrically-conductive contact plates 442, 444; 452, 454; and 462, 464 disposed on one side of housing 410. First and second pairs of contact plates 442, 444 and 452, 454 are disposed towards the proximal end of housing 410, while the third pair of contact plates 462, 464 is disposed towards the distal end of housing 410. Plates 442, 444; 452, 454; and 462, 464 are embedded within the internal surface of housing 410 that defines passageway 412 and are exposed within passageway 412. Further, one of the plates of each pair, e.g., plates 442, 452, 462, includes a contact arm 446, 456, 466, respectively, electrically coupled thereto. Contact arms 446, 456, 466 extend to a free end 448, 458, 468, respectively, that is resiliently biased away from the corresponding plates 444, 454, 464 of the pair. Contact arms 446, 456, 466 may further include humps 449, 459, 469, respectively, to facilitate urging of free ends 448, 458, 468 of contact arms 446, 456, 466, respectively, against their bias and into contacts with the corresponding plate 444, 454, 464 of the pair to electrically couple the adjacent paired plates 442, 444; 452, 454; and 462, 464 to one another via the contact arm 446, 456, 466, respectively, extending therebetween.

Continuing with reference to FIGS. 7 and 8A-8B, each contact plate 442, 444; 452, 454; and 462, 464 includes a wire (or wires) 443, 445; 453, 455; and 463, 465, respectively, electrically coupled thereto and extending therefrom. First through sixth wires 443, 445, 453, 455, 463, 465 are configured similarly to the first through sixth wires 346, 348, 356, 358, 366, 368 of switch assembly 300 (see FIGS. 5 and 6A-6B), detailed above.

In use, switch assembly 400 functions similar to switch assembly 300 (FIGS. 5 and 6A-6B). More specifically, for use in the bipolar mode of operation, as shown in FIG. 8A, slider(s) 62 are moved to the proximal position such that monopolar assembly 200 is disposed in the retracted position (see also FIGS. 2A and 4A-4C). In this position, switch assembly 400 is disposed in the first condition wherein base member 416 is positioned such that protrusion 420 urges hump 449 of arm 446 towards plates 442, 444 such that free end 448 of contact arm 446 is maintained in contact with plate 444, thereby electrically coupling plates 442, 444 to one another. Likewise, in the first condition, protrusion 430 urges hump 459 towards contact plates 452, 454 such that free end 458 of contact arm 456 is maintained in contact with plate 454, thereby electrically coupling plates 452, 454 to one another. Thus, in the proximal position of slider(s) 62, generator "G" and activation assembly 90 are electrically coupled to electrically-conductive plates 112, 122 of jaw members 110, 120, respectively and are decoupled from energizable rod member 220 of monopolar assembly 200.

With respect to the operation of forceps 10 (incorporating switch assembly 400) in the monopolar mode of operation, monopolar assembly 200 is translated from the retracted position (FIGS. 2A and 4B) to the deployed position (FIGS. 2B and 4D) via movement of either or both sliders 62 from the proximal position to the distal position. As sliders 62 are translated distally to the position shown in FIG. 8B, base member 416 is translated distally though housing 410 of switch assembly 400 from a position adjacent contact arms 446, 456 to a position adjacent contact arm 466. As such, contact arms 446, 456, no longer urged towards contact plates 444, 454, respectively, are returned under bias to spaced-apart positions with respect to contact plates 444, 454, respectively, thus decoupling end effector assembly 100 from generator "G" and activation assembly 90. Upon reaching the distal position (FIG. 8B), base member 416 is positioned such that protrusion 430 (or protrusion 420) urges hump 469 of contact arm 466 towards plates 462, 464 such that free end 468 of contact arm 466 is maintained in contact with contact plate 464, thereby electrically coupling contact plates 462, 464 to one another. In this second condition of switch assembly 400, generator "G" and activation assembly 90 are coupled to energizable rod member 220 of monopolar assembly 200 for supplying energy thereto. In some embodiments, protrusion 420 and humps 449, 459 may be provided in a stepped, offset, or other configuration to inhibit the momentary coupling of plates 452, 454 as base member 416 is translated distally through housing 410. Similar stepping or offsetting for the same purpose may also be provided with respect to switch assembly 300 (FIG. 6).

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method, comprising:
providing a surgical instrument including a bipolar connector adapted to connect to a bipolar energy source, a monopolar connector adapted to connect to a monopolar energy source, a bipolar assembly, and a monopolar assembly including an energizable portion and an insulative portion; and
moving the monopolar assembly towards a deployed position such that the insulative portion at least partially covers the bipolar assembly and such that the energizable portion extends from the insulative portion and the bipolar assembly, wherein moving the monopolar assembly towards the deployed position decouples the bipolar assembly from the bipolar connector and couples the monopolar assembly to the monopolar connector.

2. The method according to claim 1, further comprising, moving the monopolar assembly towards a retracted position, wherein moving the monopolar assembly towards the retracted position decouples the monopolar assembly from the monopolar contact and couples the bipolar assembly to the bipolar contact.

3. The method according to claim 2, wherein moving the monopolar assembly towards the retracted position includes moving the insulative portion towards a retracted position such that the insulative portion is disposed proximally of the bipolar assembly.

4. The method according to claim 2, wherein moving the monopolar assembly towards the retracted position includes moving an energizable rod of the monopolar assembly into an insulated lumen defined within the bipolar assembly.

5. The method according to claim 2, further comprising, with the monopolar assembly disposed in the retracted position, supplying bipolar energy to the bipolar assembly via the bipolar connector for conducting bipolar energy through tissue to treat tissue.

6. The method according to claim 5, wherein conducting bipolar energy through tissue to treat tissue includes conducting energy between first and second electrically-conductive plates of the bipolar assembly to seal tissue disposed therebetween.

7. The method according to claim 1, further comprising, with the monopolar assembly disposed in the deployed position, supplying monopolar energy to the monopolar assembly via the monopolar connector for applying monopolar energy to tissue to treat tissue.

8. The method according to claim 7, wherein applying monopolar energy to tissue to treat tissue includes applying energy from an energizable rod member of the monopolar assembly to tissue to dissect tissue adjacent the energizable rod member.

9. The method according to claim 1, wherein moving the monopolar assembly towards the deployed position includes moving the monopolar assembly against a bias of a biasing member.

10. The method according to claim 1, further comprising moving the monopolar assembly towards an intermediate position, wherein moving the monopolar assembly towards the intermediate position decouples the bipolar assembly from the bipolar connector and maintains the monopolar assembly decoupled from the monopolar connector.

11. The method according to claim 10, wherein the intermediate position of the monopolar assembly is disposed between a retracted position and the deployed position such that the monopolar assembly is moved through the intermediate position upon movement of the monopolar assembly between the retracted position and the deployed position.

12. A method, comprising:
providing a first bipolar input adapted to connect to a bipolar source of energy, a second bipolar input adapted to connect to the bipolar source of energy, a first bipolar output coupled to a first bipolar energizable member, a second bipolar output coupled to a second bipolar energizable member, a monopolar input adapted to connect to a monopolar source of energy, and a monopolar output coupled to a monopolar energizable member, the monopolar energizable member including an insulative portion associated therewith;

moving the monopolar energizable member towards a deployed position such that the insulative portion at least partially covers the first bipolar energizable member and the second bipolar energizable member and such that the monopolar energizable member extends from the first bipolar energizable member, the second bipolar energizable member, and the insulative portion, wherein moving the monopolar energizable member towards the deployed position decouples the first bipolar input and the second bipolar input from the first bipolar output and the second bipolar output, respectively, and couples the monopolar input to the monopolar output.

13. The method according to claim 12, further comprising, moving the monopolar energizable member towards a retracted position, wherein moving the monopolar energizable member towards the retracted position decouples the monopolar input from the monopolar output and couples the first bipolar input and the second bipolar input to the first bipolar output and the second bipolar output, respectively.

14. The method according to claim 13, wherein moving the monopolar energizable member towards the retracted position includes moving the insulative portion towards a retracted position such that the insulative portion is disposed proximally of the first energizable member and the second energizable member.

15. The method according to claim 13, further comprising, with the monopolar energizable member disposed in the retracted position, supplying bipolar energy to the first energizable member and the second energizable member via the first bipolar input and the second bipolar input, respectively, for conducting bipolar energy through tissue to treat tissue.

16. The method according to claim 15, wherein conducting bipolar energy through tissue to treat tissue includes conducting energy between the first energizable member and the second energizable member to seal tissue disposed therebetween.

17. The method according to claim 12, further comprising, with the monopolar energizable member disposed in the deployed position, supplying monopolar energy to the monopolar energizable member via the monopolar input for applying monopolar energy to tissue to treat tissue.

18. The method according to claim 17, wherein applying monopolar energy to tissue to treat tissue includes applying energy from the monopolar energizable member of the monopolar assembly to tissue to dissect tissue adjacent the third energizable member.

19. The method according to claim 12, further comprising moving the monopolar energizable member towards an intermediate position, wherein moving the monopolar energizable member towards the intermediate position decouples the first bipolar input and the second bipolar input from the first bipolar output and the second bipolar output, respectively, and maintains the monopolar input decoupled from the monopolar output.

20. The method according to claim 19, wherein the intermediate position of the monopolar energizable member is disposed between a retracted position and the deployed position such that the monopolar energizable member is moved through the intermediate position upon movement of the monopolar energizable member between the retracted position and the deployed position.

* * * * *